United States Patent
Eichenseer

(10) Patent No.: US 10,568,674 B1
(45) Date of Patent: Feb. 25, 2020

(54) PEDICLE SCREWS WITH INTEGRATED ANCHOR FOR RETAINING ARTIFICIAL LIGAMENT TAPE USED FOR POSTERIOR LIGAMENT RECONSTRUCTION

(71) Applicant: Syberspine Limited, New Albany, OH (US)

(72) Inventor: Paul H. Eichenseer, New Albany, OH (US)

(73) Assignee: Syberspine Limited, New Albany, OH (US)

( * ) Notice: Subject to any disclaimer, the term of this patent is extended or adjusted under 35 U.S.C. 154(b) by 0 days.

(21) Appl. No.: 16/256,618

(22) Filed: Jan. 24, 2019

(51) Int. Cl.
*A61B 17/70* (2006.01)
*A61B 17/86* (2006.01)
*A61B 17/68* (2006.01)

(52) U.S. Cl.
CPC ...... *A61B 17/8605* (2013.01); *A61B 17/7032* (2013.01); *A61B 17/8625* (2013.01); *A61B 17/686* (2013.01); *A61B 17/7007* (2013.01); *A61B 17/7022* (2013.01); *A61B 17/8665* (2013.01)

(58) Field of Classification Search
CPC .................................................. A61B 17/7053
See application file for complete search history.

(56) References Cited

U.S. PATENT DOCUMENTS

| | | | |
|---|---|---|---|
| 5,180,393 A | 1/1993 | Commarmond | |
| 5,425,767 A | 6/1995 | Steininger et al. | |
| 6,576,017 B2 | 6/2003 | Foley et al. | |
| 8,034,083 B2 | 10/2011 | Abdelgany et al. | |
| 8,070,785 B2 | 12/2011 | Biscup | |
| 2014/0257397 A1* | 9/2014 | Akbarnia | A61B 17/8869 606/263 |
| 2018/0078286 A1* | 3/2018 | Le Couedic | A61B 17/7043 |

FOREIGN PATENT DOCUMENTS

WO  WO-2016166448 A1 * 10/2016  ......... A61B 17/7043

OTHER PUBLICATIONS

Jazz Lock—Posterior fixation system of the spine, pp. 1-13, Implanet, Martillac, France—Implanet America, Inc., Boston, MA.
Surgical Technique Band Connector—Ligapass 2.0, pp. 1-15, Medicrea.
Songer Spinal Cable System—Surgical Technique, 2009, pp. 1-18, Pioneer Surgical Technology, Marquette, MI.

* cited by examiner

*Primary Examiner* — Samuel S Hanna
(74) *Attorney, Agent, or Firm* — Frank H. Foster; Kremblas & Foster

(57) ABSTRACT

A pedicle screw of the type used in spinal fixation surgery has integral structure for anchoring artificial ligament tape. A tape-receiving passageway is formed through the tulip assembly of the pedicle screw. The passageway has open ends and is configured to receive an artificial ligament tape threaded through the passageway. An opening is formed in the tulip assembly, transversely intersecting the passageway and opening to the exterior of the tulip assembly. A clamping member is movable along the opening into clamping engagement against a segment of the artificial ligament tape that is threaded through the passageway.

6 Claims, 5 Drawing Sheets

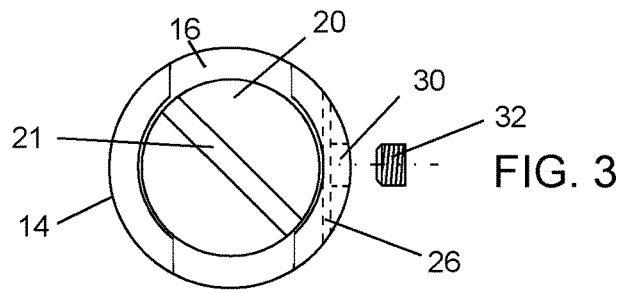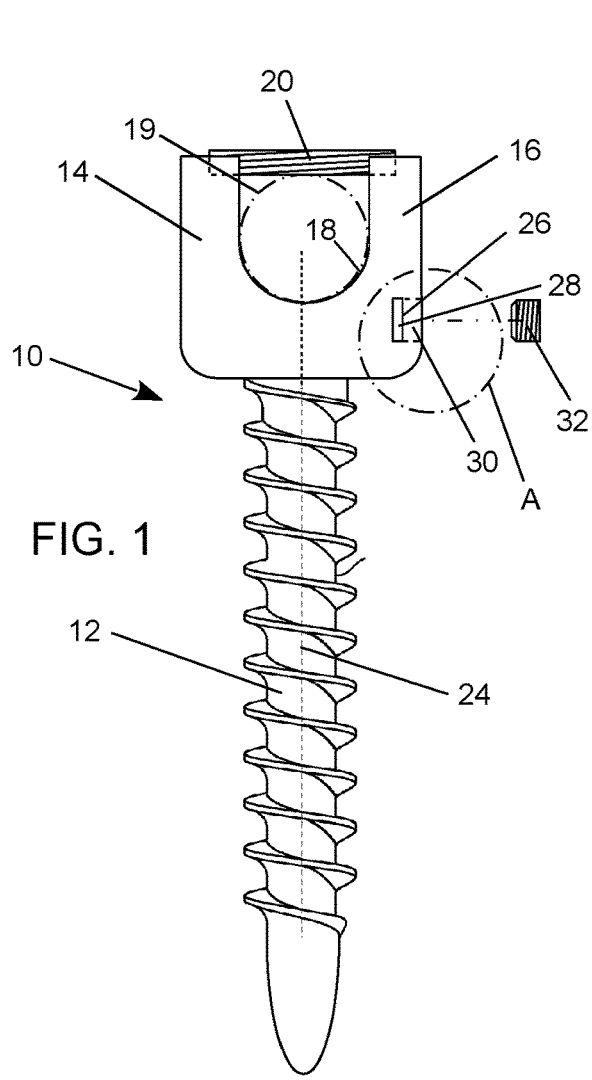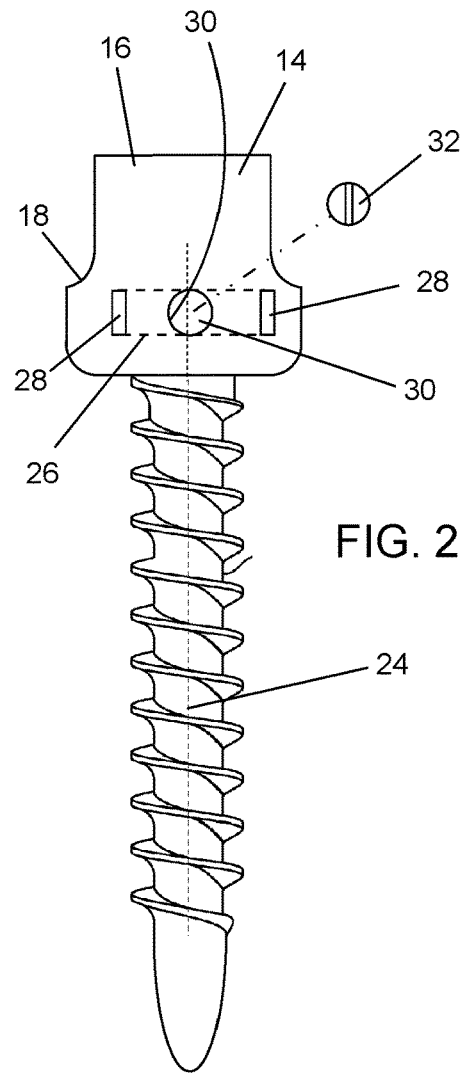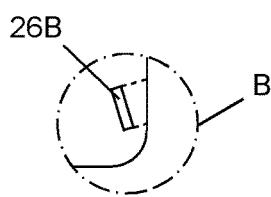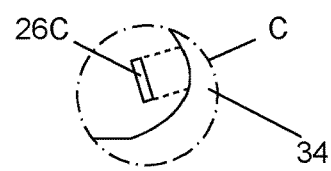

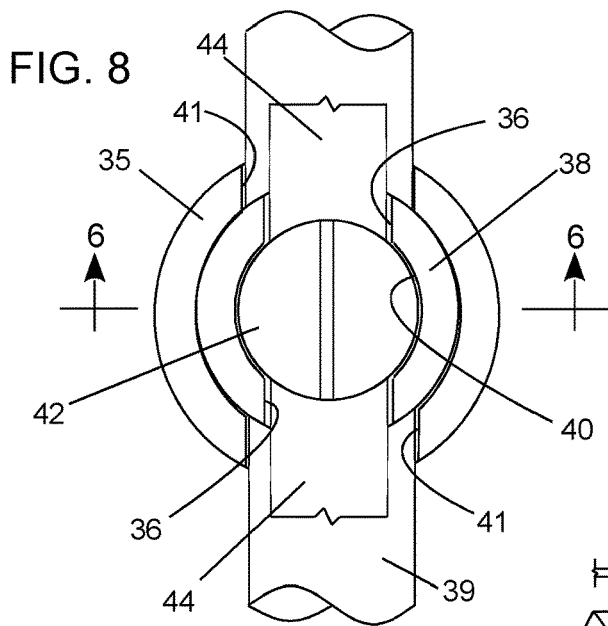
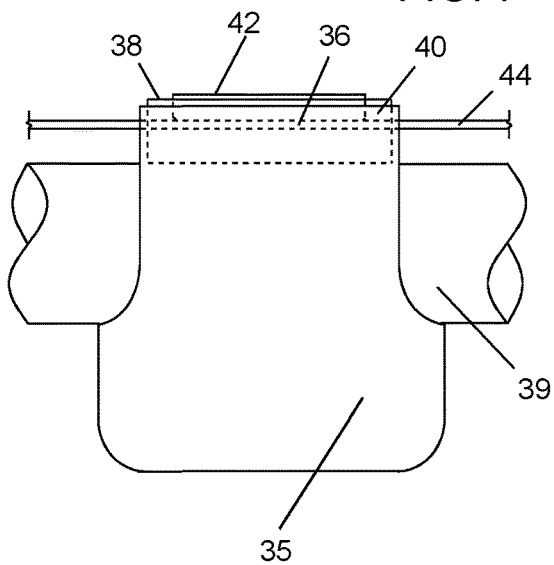
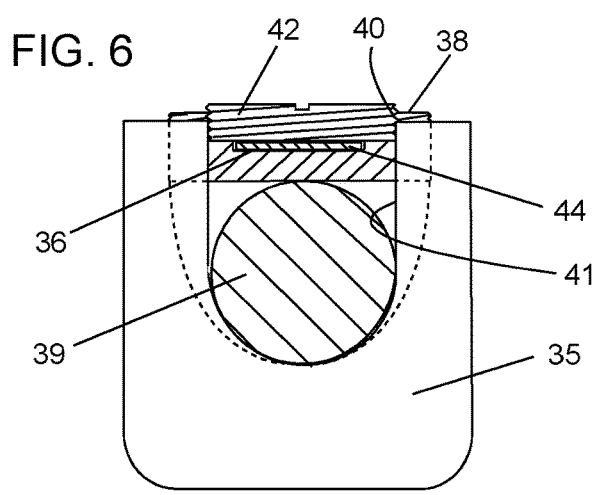
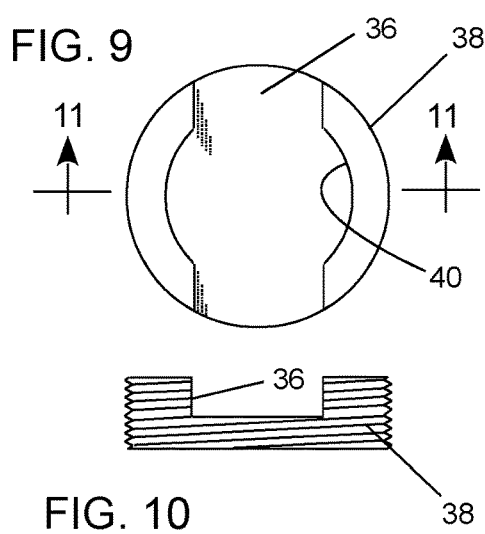
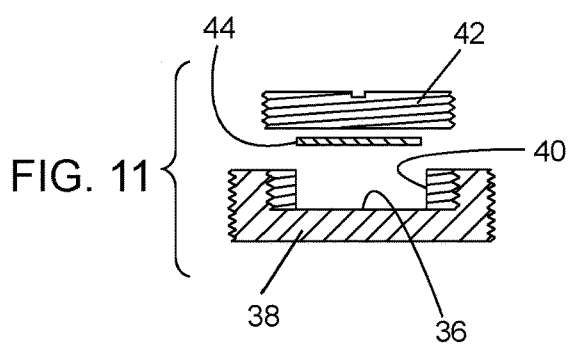

FIG. 12
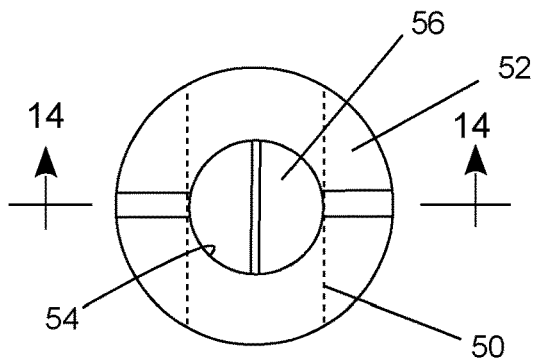
FIG. 13
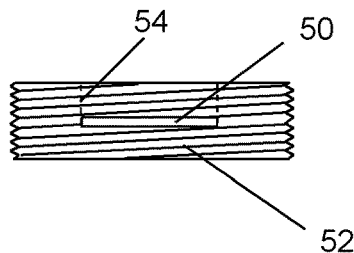
FIG. 14
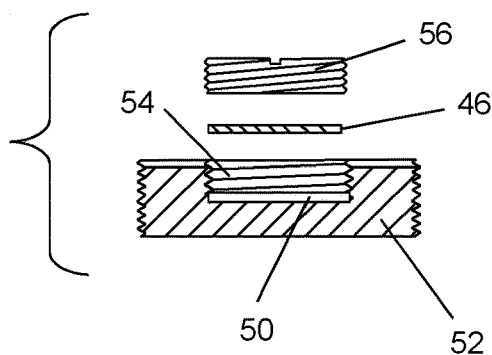
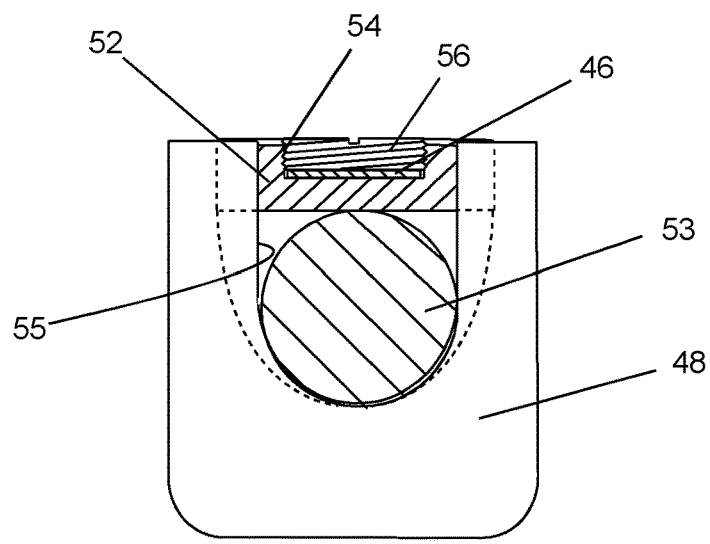
FIG. 15

FIG. 16
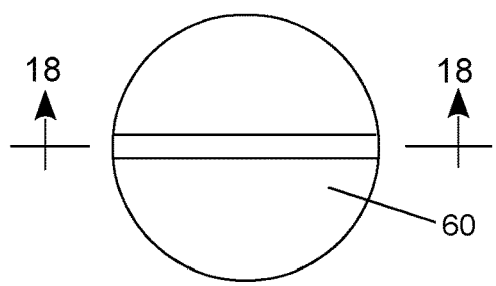
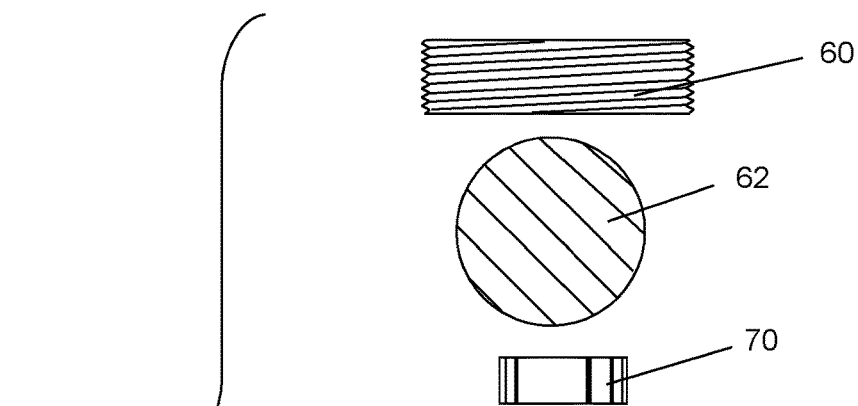
FIG. 17
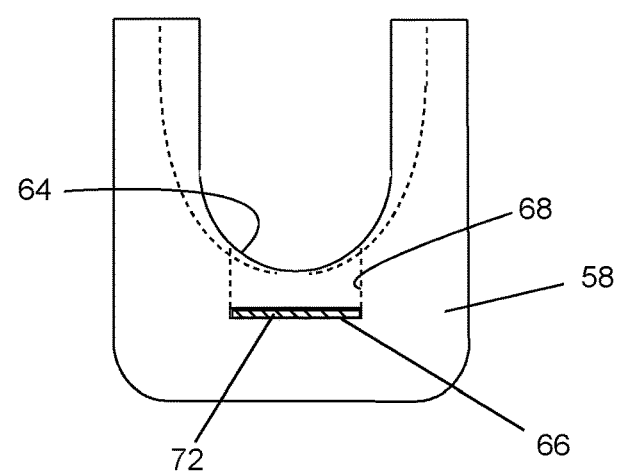
FIG. 18
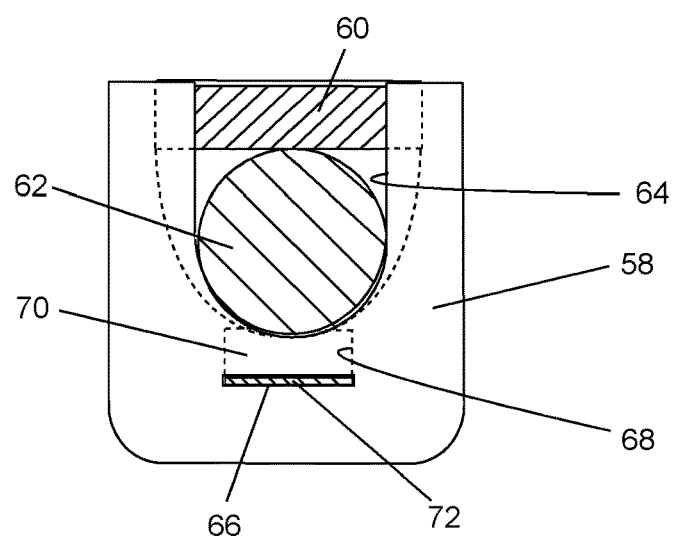

PEDICLE SCREWS WITH INTEGRATED ANCHOR FOR RETAINING ARTIFICIAL LIGAMENT TAPE USED FOR POSTERIOR LIGAMENT RECONSTRUCTION

BACKGROUND OF THE INVENTION

This invention is directed to implants used in spinal fixation surgery and more particularly is directed to means for anchoring artificial ligament tape in a construct for tethering an uppermost fused vertebra to higher vertebrae.

The prior art discloses a variety of structures and methods for treating one or more degenerated, deformed or damaged vertebral stages of a patient's spinal column by means of internal spinal fixation. Typically, this involves the attachment of a spinal implant system to provide a construct that is attached to two or more adjacent vertebrae to support and stabilize the vertebrae in order to allow them to fuse together in a stationary relationship relative to each other. Spinal fusion constructs typically include pedicle screws and longitudinal support members or rods that are attached to the pedicle screws and together they fix the position of the adjacent vertebrae to which they are attached.

However, a problem that develops after surgery in many patients as a result of patient activity or stature is that the vertebra that is immediately above the highest fused vertebra breaks away from the highest fused vertebra and falls forward. Surgeons sometimes attempt to prevent that problem by securing vertebrae that are immediately above the uppermost instrumented vertebra to the uppermost instrumented vertebra by means of artificial ligament tape. (An instrumented vertebra is a vertebra to which a device is implanted or connected.)

One way of doing this is to first drill a hole through the spinous process of the uppermost instrumented vertebra and also the contiguous vertebrae that are immediately above the uppermost instrumented vertebra and are to be secured by the ligament tape. The ligament tape is then threaded through the drilled holes upward from the uppermost instrumented vertebra to the higher vertebrae and then threaded back down again through the holes to the uppermost instrumented vertebra. In one procedure the ligament tape is then pulled in tension and tied to itself or to one or two of the rods that are a part of the construct. Unfortunately, this procedure often results in a loosening of the ligament tape because much of the tension is lost during the manipulation of the ligament tape into a knot and also because the tape can loosen further after surgery from slippage of the knot.

In order to reduce this loosening problem, the prior art has provided specialized anchoring devices that are attached to the construct and allow the surgeon to fasten the ligament tape to the construct. These specialized anchoring devices avoid the use of a knot and also allow a greater tension to be maintained while the tape is being secured to the anchors and thereby reduce or eliminate later slippage at the anchor. However, these specialized anchoring devices result in a construct that adds them as one or more additional devices that must be included in the construct. The additional devices increase the space occupied by the construct, require additional manipulation by the surgeon, must be taken into account when closing the wound and increase cost.

It is therefore an object and feature of the invention to provide a structure for anchoring the artificial ligament tape without requiring the surgeon to mount any additional specialized anchoring devices on the support rods or any other part of the construct.

The term "artificial ligament tape" is used in a generic sense to refer to a type of cordage that is available for surgeons to perform the procedures that are described above. Some prior art refers to equivalent structures as tape, cable, rope, tether, wire, braid, band or strand. They are an elongated structure that is flexible so that they bend easily (with the application of relatively little force) but also have a strong resistance to being stretched longitudinally by a substantial pulling force. Other equivalent terms include artificial ligament reconstruction tape, Mersilene tape and TLS® strips.

BRIEF SUMMARY OF THE INVENTION

The basic concept of the invention is to provide a structure which can be included as an integral part of a pedicle screw and to which an artificial ligament tape can be anchored. As a result, a construct that uses a pedicle screw will not require an additional, dedicated, special purpose anchor. Instead pedicle screws can be installed in their usual manner but will serve both their conventional purpose, as widely described in the prior art, and also serve as anchors for an artificial ligament tape.

A ligament tape-receiving passageway is formed through the tulip assembly of a pedicle screw. The passageway has open ends and is configured to receive an artificial ligament tape threaded through the passageway. An opening is formed in the tulip assembly, transversely intersecting the passageway and opening at one end to the passageway and at its opposite end to the exterior of the tulip assembly. A clamping member is movable along the opening into clamping engagement against a segment of the artificial ligament tape that is threaded through the passageway.

BRIEF DESCRIPTION OF THE SEVERAL VIEWS OF THE DRAWINGS

FIG. 1 is a view in front elevation of an embodiment of the invention.

FIG. 2 is a side view of the embodiment illustrated in FIG. 1.

FIG. 3 is a top view of the embodiment illustrated in FIG. 1.

FIG. 4 is a partial side view showing an alternative segment of the embodiment of FIGS. 1-3.

FIG. 5 is a partial side view showing another alternative segment of the embodiment of FIGS. 1-3.

FIG. 6 is a front view of an alternative embodiment of the invention and is partially in section taken along the line 6-6 of FIG. 8.

FIG. 7 is a side view of the embodiment of FIG. 6.

FIG. 8 is a top view of the embodiment of FIG. 6.

FIG. 9 is a top view of the primary set screw of the embodiment of FIG. 6.

FIG. 10 is a side view of the primary set screw of FIG. 9.

FIG. 11 is a top view of the primary set screw, the artificial ligament tape and the secondary set screw of the embodiment of FIG. 6.

FIG. 12 is an exploded view of the primary set screw and the secondary set screw of another embodiment of the invention illustrated in FIGS. 12-15.

FIG. 13 is a side view of the primary set screw illustrated in FIG. 12.

FIG. 14 is an exploded view of the primary set screw, artificial ligament tape and secondary set screw of the embodiment of the invention illustrated in FIGS. 12-15 and partially in section taken along the line 14-14 of FIG. 12.

FIG. 15 is a side view of the embodiment of FIGS. 12-15 partially in section taken along the line 14-14 of FIG. 12.

FIG. 16 is a top view of the primary set screw of yet another embodiment of the invention illustrated in FIGS. 16-18.

FIG. 17 is an exploded view of the embodiment of the invention illustrated in FIGS. 16-18.

FIG. 18 is a side view of the embodiment of the invention illustrated in FIGS. 16-18 and partially in section taken along the line 18-18 of FIG. 16.

DETAILED DESCRIPTION OF THE INVENTION

Figure 19:
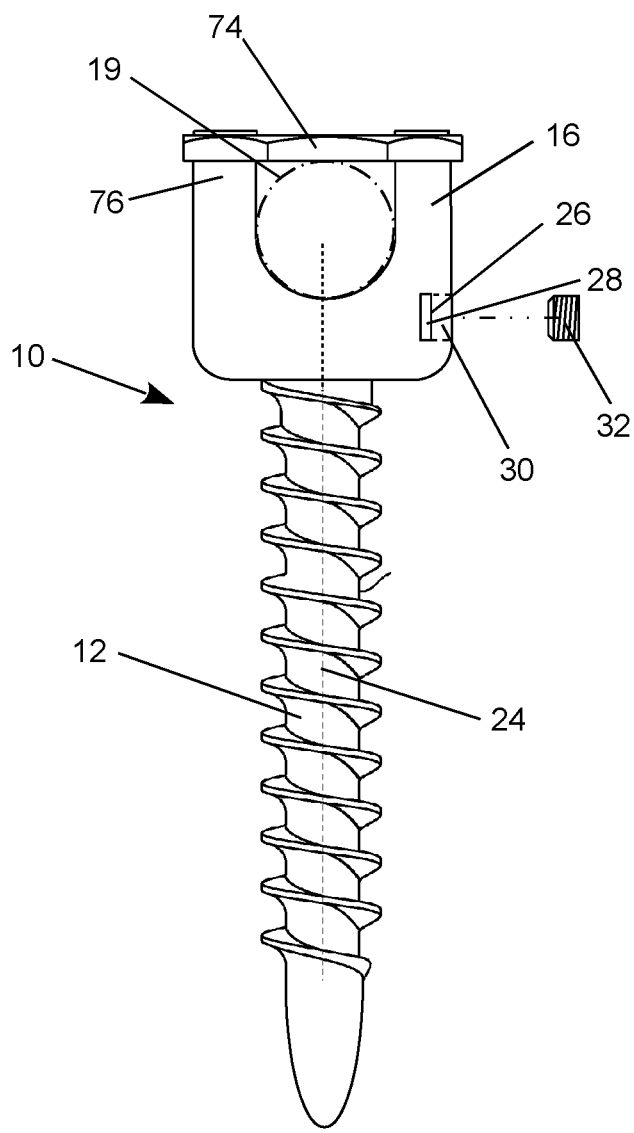
FIG. 19 is a view in front elevation of an alternative embodiment of the invention that utilizes a prior art primary nut that engages an exterior wall of the tulip instead of a primary set screw for clamping a rod against the bottom surface of the U-shaped slot of the saddle In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

Referring to the drawings, FIGS. 1-3 illustrate a first embodiment of the invention and the description of it begins with a description of the conventional, prior art structural features of typical, common pedicle screws. A pedicle screw 10 has a threaded screw shank 12 mounted to a tulip assembly 14. The tulip assembly 14 includes a tulip head 16 having a slot forming a saddle 18 for receipt of a longitudinal spinal support rod 19. The saddle 18 is the surface of the slot that is aligned diametrically across the tulip head 16 and is contoured to seat against the rod 19 with mating interfacing contours.

The tulip assembly 14 also includes a primary set screw 20 that threadedly engages the interior wall of the saddle 18 and has a tool slot 21. The primary set screw 20 moves axially when rotated for clamping a rod 19 against the bottom of the saddle 18. An alternative tulip assembly (illustrated in FIG. 19) of some prior art pedicle screws has a primary nut member 74 that threadedly engages the outer surface 76 of the tulip head 16. Like a primary set screw, a nut member moves axially when rotated for clamping the rod against the bottom of the saddle. Another alternative prior art nut member, when rotated, drives a central bar downward to clamp against a rod to secure the rod in the saddle. With one type of alternative nut-type pedicle screw, the nut is formed like a cap with the bar integrally formed centrally on the underside of the cap and extending into the saddle. With another type of alternative nut-type pedicle screw the bar has diametrically opposite short arms that extend into the slots at the opposite ends of the saddle so that the nut, when rotated, will drive the bar against the rod.

The term "primary set screw" is used in this description as the broad generic term for the part of the tulip assembly 14 that moves axially when rotated to move further into the saddle in order to clamp a support rod against the bottom of the saddle. The term includes structures that use other than conventional threads, such as inclined grooves on opposite sides of the saddle and an internal screw with outward extending tabs that extend into the grooves for moving into the saddle when rotated. Such structures may be referred to as a twist lock. The term also includes tulip assemblies that use a surrounding nut that is threadedly engaged to the exterior of the tulip assembly and an interior disk with diametrically opposite arms that extend outwardly through the open ends of the saddle so the arms are contacted by the nut and the disk is driven against the rod when the nut is rotated.

As illustrated in FIGS. 1 and 2, the tulip assembly 14 has a longitudinal axis 24. The tulip assembly often has a variety of additional parts depending upon the design of various manufacturers and depending upon whether the pedicle screw is a monoaxial or a polyaxial pedicle screw. With a polyaxial pedicle screw, the tulip swivels on its threaded shank to help defray vertebral stress and is fixed in position when the rod is clamped in place in the saddle. The figures illustrate a monoaxial pedicle screw but the various embodiments of the invention are also applicable to polyaxial pedicle screws, though not necessarily all. Of course with a polyaxial pedicle screw the longitudinal axis 24 moves with the tulip assembly 14.

The foregoing description describes conventional prior art pedicle screws and their components. The structural features of the invention are next described.

Referring still to FIGS. 1-3, a ligament tape-receiving passageway 26 is formed through the tulip assembly 14 and has open opposite ends 28. The passageway 26 is configured to receive an artificial ligament tape that is threaded by the surgeon through the passageway 26. Preferably in this embodiment the passageway 26 is a hole through the tulip head 16 but, as will be seen, the tape-receiving passageway can be a channel in some embodiments.

An opening 30 in the tulip assembly 14 transversely, and preferably perpendicularly, intersects and opens into the passageway 26 and also opens at its opposite end to the exterior of the tulip assembly 14. A clamping member 32 is configured to be movable along the opening 30 into clamping engagement against a segment of an artificial ligament tape that is threaded through the passageway 26. Preferably, the clamping member 32 is a secondary set screw that is threadedly engaged within the opening 30 so that it can be rotated by a tool to be advanced along the opening into engagement against the ligament tape to secure the tape in position where it is tightly anchored to the pedicle screw 10.

There are various preferred and alternative structural variations of the embodiment illustrated in FIGS. 1-3. The tape-receiving passageway 26 does not necessarily intersect the axis 24. Preferably, the tape-receiving passageway 26 is aligned transversely across the tulip assembly and most preferably is perpendicularly oriented with respect to the longitudinal axis 24. Cordage that is used for the procedures described above is commonly available in forms that have a circular or a rectangular cross section. For use with cordage with a circular cross section, commonly referred to as cable or wire, the passageway 26 may preferably have a circular cross section. Similarly, for cordage with a rectangular cross section, such as commonly referred to as a tape or band, the passageway 26 preferably has a rectangular cross section. Cordage with other cross sectional configurations may have correspondingly configured passageways 26. For any passageway, it is desirable that the opposite ends of the passageway be smoothed and rounded to avoid having the ligament tape in contact with a sharp edge.

FIGS. 4 and 5 illustrate alternative configurations for the passageway 26. Those figures show alternative drawing segments B and C that can be substituted for the segment A of FIG. 1. In FIG. 4, the rectangular passageway 26B is inclined with respect to the longitudinal axis 24. FIG. 5 shows that, in addition to having an inclined, passageway 26C, a skirt 34 or potbelly protrusion may be added to the tulip head 16 outward of the inclined passageway 26C. The inclined rectangular passageways 26B and 26C have major and minor axes that are inclined at an acute angle to the central axis 24. Inclining the passageway for the artificial ligament tape is not necessary but it facilitates inserting and threading the ligament tape along the passageway. The reason is that soft tissue surrounds the entire construct so the visibility of the construct and access to it is obstructed by the surrounding soft tissue. Consequently the surgeon is confined to working straight down or at an angle. It is difficult or impossible to approach the construct with a tool in a direction that is directly from the left or right parallel to the coronal plane and perpendicular to the central axis of tulip assembly 14. Inclining the passageway in the manner described allows the opening 30 for the clamping member/set screw 32 to be inclined to the coronal plane. This inclination permits the surgeon to approach and obtain access to the set screw 32 (i.e. with a tool for rotating the clamping member/set screw 32) in a direction that is inclined with respect to the coronal plane.

FIGS. 6 through 11 illustrate another embodiment of the invention applied to a tulip assembly 35. Referring to those figures, a ligament tape-receiving passageway 36 is formed as a channel 36 across an outwardly facing end of a primary set screw 38. The primary set screw 38 is used to clamp a support rod 39 in the saddle 41 in the tulip assembly 35 in the conventional manner. An opening 40 for receiving a clamping member 42 is a threaded segment 40 of channel 36 sidewalls. The clamping member 42 is a secondary set screw 42 that is threadedly engaged in the threaded segment 40 of the channel 36. The secondary set screw 42 is configured to advance into the threaded segment 40, and therefore into the channel 36, and seat against an artificial ligament tape 44 in the channel 36, by rotation of the secondary set screw 42.

FIGS. 12 through 15 illustrate yet another alternative embodiment of the invention for anchoring an artificial ligament tape 46 to a tulip assembly 48. In this embodiment a ligament tape-receiving passageway 50 is formed as a partially enclosed hole 50 extending through the primary set screw 52 with opposite open ends. The hole 50 extends completely, transversely and preferably diametrically through the primary set screw 52. The primary set screw 52 is also used to clamp a support rod 53 in the saddle 55 in the tulip assembly 48 in the conventional manner.

An opening 54 for receiving a clamping member 56 is a threaded hole 54 into an outwardly facing end of the primary set screw 52. The clamping member 56 is formed by a secondary set screw 56 that is threadedly engaged in the threaded opening 54. The secondary set screw 56 is configured to advance into the opening 54 and against the artificial ligament tape 46 in the passageway 50 by rotation of the secondary set screw 56.

Still another embodiment of the invention is illustrated in FIGS. 16 through 18. In this embodiment a tulip assembly 58 has a primary set screw 60 that is used in the conventional manner for clamping a support rod 62 in the saddle 64. A ligament tape-receiving passageway 66 is a hole 66 entirely through the tulip assembly 58. The ligament tape-receiving passageway 66 is spaced from the saddle 64 and below the saddle 64 in the orientation of the tulip assembly 58 that is shown in the drawings. An opening 68 for receiving a clamping member 70 is a bore 68 extending between the base of the saddle 64 and the ligament tape-receiving passageway 66. A clamping member 70 is formed by a push bar 70 that is slidable along the bore 68 and preferably formed as a disk. The push bar 70 is pushed in a direction toward and into the passageway 66 and against an artificial ligament tape 72 by the rod 62 when the rod 62 is clamped in the saddle 64 by rotation of the primary set screw 60. The single step of rotating the primary set screw 60 both clamps the rod 62 in the saddle 64 and anchors the artificial ligament tape 72 to prevent the tape 72 from sliding within the passageway 66.

The push bar 70 must be sufficiently longer than the opening 68 so that it will be held against the artificial ligament tape 72 with sufficient force to securely anchor the tape 72 in the tulip assembly 58. Preferably the push bar 70 is formed either from a sufficiently stiff but elastic, resiliently compressible material or a malleable material such as commercially pure titanium. With this embodiment, after the artificial ligament tape 72 is threaded through the tape-receiving passageway 66 and pulled tight, the primary set screw 60 is rotated to tighten it down into the saddle 64 and against the rod 62. The rod 62 clamps down onto the push bar 70 and forces it into the tape-receiving passageway 66 and against the artificial ligament tape 72. If the push bar 70 is elastic or malleable, it becomes deformed from the force applied as a result of rotating the primary set screw.

With all the embodiments of the invention, the surgeon installs the pedicle screws and assembles the construct in the usual manner. Ordinarily, each vertebral body will have two pedicle screws, one in each of its pedicles. The artificial ligament tape is then threaded from an uppermost vertebra or vertebra above the construct and back down again in the customary manner as previously described to tether the upper portion of the spine to the construct. The two ends of the tapes are then threaded through the tape-receiving passageways in the tulip assembly of the chosen pedicle screws.

From the above it can be appreciated that the invention provides two new advantages. First, when an embodiment of the invention is used, there are no additional devices to be installed in the construct. Therefore a construct is provided that does not occupy additional space or additional volume. Although there are no additional devices, the disadvantage of tying the artificial ligament tape to itself by a knot are avoided. The advantages of anchoring the artificial ligament tape to the construct is attained by allowing the artificial ligament tape to be pulled and held taught while the clamping member is rotated and tightened against the artificial ligament tape to anchor it to the construct.

REFERENCE NUMBER KEY

- 10 pedicle screw (FIGS. 1-3)
- 12 screw shank of pedicle screw (FIGS. 1-3)
- 14 tulip assembly (FIGS. 1-3)
- 16 tulip head (FIGS. 1-3)
- 18 saddle of tulip head (FIGS. 1-3)
- 19 rod (FIGS. 1-3)
- 20 primary set screw (FIGS. 1-3)
- 21 tool slot (FIGS. 1-3)
- 22 longitudinal support rod (FIGS. 1-3)
- 24 longitudinal axis of tulip assembly (FIGS. 1-3)
- 26 ligament tape-receiving passageway (FIGS. 1-3)
- 28 open ends of passageway (FIGS. 1-3)
- 30 opening (FIGS. 1-3)
- 32 clamping member (FIGS. 1-3)
- 34 skirt (FIG. 5)
- 35 tulip assembly (FIGS. 6-11)
- 36 ligament tape-receiving passageway (FIGS. 6-11)
- 38 primary set screw (FIGS. 6-11)
- 39 support rod (FIGS. 6-11)
- 40 opening/channel (FIGS. 6-11)
- 41 saddle (FIGS. 6-11)

42 clamping member/secondary set screw (FIGS. 6-11)
44 artificial ligament tape (FIGS. 6-11)
46 artificial ligament tape (FIGS. 12-15)
48 tulip assembly (FIGS. 12-15)
50 ligament tape-receiving passageway (FIGS. 12-15)
52 primary set screw (FIGS. 12-15)
53 support rod (FIGS. 12-15)
54 opening for receiving clamping member/set screw (FIGS. 12-15)
55 saddle (FIGS. 12-15)
56 clamping member/secondary set screw (FIGS. 12-15)
58 tulip assembly (FIGS. 16-18)
60 primary set screw (FIGS. 16-18)
62 support rod (FIGS. 16-18)
64 saddle (FIGS. 16-18)
66 ligament tape-receiving passageway (FIGS. 16-18)
68 opening for receiving clamping member/bore (FIGS. 16-18)
70 clamping member/push bar (FIGS. 16-18)
72 artificial ligament tape (FIGS. 16-18)

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. An improved pedicle screw including a threaded screw shank mounted to a tulip assembly, the tulip assembly including a tulip head having cylindrically contoured peripheral sides and including a U-shaped slot forming a saddle for receipt of a spinal support rod and the tulip assembly also including a primary set screw that engages an interior wall of the saddle or a primary nut that engages an exterior wall of the tulip assembly, the primary set screw or nut moving axially when rotated for clamping the rod against a bottom surface of the U-shaped slot of the saddle, wherein the tulip head additionally comprises:
 (a) a ligament tape-receiving passageway formed through the tulip head, spaced on a side from the slot, extending parallel to the slot between opposite peripheral sides of the tulip head and terminating at opposite open ends located at an outer peripheral surface of the tulip head no further outward than the cylindrically contoured peripheral sides of the tulip head, the passageway not intersecting the slot and configured to receive an artificial ligament tape threaded through the passageway parallel to the support rod;
 (b) an opening in the tulip head, transversely intersecting the passageway, not intersecting the slot and opening to the exterior of the tulip head; and
 (c) a clamping member that is movable within the tulip head along the opening into clamping engagement against a segment of the artificial ligament tape threaded through the passageway.

2. A pedicle screw in accordance with claim 1 wherein the tulip head has a longitudinal axis and the passageway is aligned across the tulip head transversely with respect to the longitudinal axis.

3. A pedicle screw in accordance with claim 2 wherein the passageway is a hole through the tulip head, the opening is a threaded hole and the clamping member is a secondary set screw threadedly engaged in the opening and configured to advance along the opening and against the artificial ligament tape by rotation of the secondary set screw.

4. A pedicle screw in accordance with claim 3 wherein the passageway has a rectangular cross section.

5. A pedicle screw in accordance with claim 4 wherein the passageway is aligned at a right angle to the longitudinal axis.

6. A pedicle screw in accordance with claim 4 wherein the rectangular cross-section has a major axis and a minor axis, and the major and minor axes are inclined at an acute angle to the longitudinal axis.

* * * * *